United States Patent
O'Rourke et al.

(10) Patent No.: US 10,151,633 B2
(45) Date of Patent: Dec. 11, 2018

(54) HIGH ACCURACY ABSORBANCE SPECTROPHOTOMETERS

(71) Applicant: Savannah River Nuclear Solutions, LLC, Aiken, SC (US)

(72) Inventors: Patrick E. O'Rourke, Martinez, GA (US); Robert J. Lascola, NA, SC (US); David Immel, Augusta, GA (US); Edward A. Kyser, III, Aiken, SC (US); Jean R. Plummer, Aiken, SC (US)

(73) Assignee: Savannah River Nuclear Solutions, LLC, Aiken, SC (US)

( * ) Notice: Subject to any disclaimer, the term of this patent is extended or adjusted under 35 U.S.C. 154(b) by 0 days.

(21) Appl. No.: 15/428,639

(22) Filed: Feb. 9, 2017

(65) Prior Publication Data

US 2018/0224334 A1 Aug. 9, 2018

(51) Int. Cl.
*G01J 3/42* (2006.01)
*G01J 3/10* (2006.01)
(Continued)

(52) U.S. Cl.
CPC ............... *G01J 3/42* (2013.01); *G01J 3/0297* (2013.01); *G01J 3/10* (2013.01); *G01J 3/427* (2013.01);
(Continued)

(58) Field of Classification Search
CPC ...... G01J 3/42; G01J 3/10; G01J 3/427; G01J 3/0297; G01J 2003/284; G01J 2003/102; G01N 21/3103
See application file for complete search history.

(56) References Cited

U.S. PATENT DOCUMENTS 3,924,950 A * 12/1975 Siegler, Jr. ......... G01N 21/3103
356/307
4,158,505 A 6/1979 Mathisen et al.
(Continued)

FOREIGN PATENT DOCUMENTS

GB 1072139 6/1967
GB 1432613 4/1976
WO WO 2015/145429 10/2015

OTHER PUBLICATIONS

Andrzej W. Miziolek and Richard J. Willis, "Saturated double-resonance emission spectroscopy of lead for sensitive atomic analysis," Opt. Lett. 6, 528-530 (1981).*
(Continued)

*Primary Examiner* — Dominic J Bologna
(74) *Attorney, Agent, or Firm* — Dority & Manning, P.A.

(57) ABSTRACT

Spectrophotometers and spectroscopy processes are described that can provide for in-line calibration at every spectral acquisition as well as for continuous response correction during sample processing. The spectrophotometers include multiple polychromatic light sources that include characteristic emission spectra for use as an internal wavelength drift calibration system that is independent of environmental factors. Correction functions provided by the internal calibration process can be applied continuously and across an entire sample spectrum. The intensity response of each spectrometer in a spectrophotometer can also be monitored and continuously corrected for stray light, dark current, readout noise, etc.

20 Claims, 4 Drawing Sheets (51) Int. Cl.
*G01N 21/31* (2006.01)
*G01J 3/427* (2006.01)
*G01J 3/02* (2006.01)
*G01J 3/28* (2006.01)

(52) U.S. Cl.
CPC .... *G01N 21/3103* (2013.01); *G01J 2003/102* (2013.01); *G01J 2003/284* (2013.01)

(56) References Cited

U.S. PATENT DOCUMENTS

| | | |
|---|---|---|
| 4,529,308 A | 7/1985 | Rife |
| 5,459,677 A | 10/1995 | Kowalski et al. |
| 5,742,399 A | 4/1998 | McAndrew et al. |
| 5,754,289 A | 5/1998 | Ozaki et al. |
| 5,777,733 A * | 7/1998 | Radziuk .......... G01J 3/2803 356/328 |
| 6,002,990 A | 12/1999 | Hanna |
| 6,552,792 B1 | 4/2003 | Pilgrim et al. |
| 7,400,398 B2 * | 7/2008 | Stedman .......... G01J 3/02 356/326 |
| 7,903,252 B2 | 3/2011 | Larsen et al. |
| 8,189,196 B2 | 5/2012 | Belz |
| 8,310,671 B1 * | 11/2012 | Nguyen .......... G01J 3/44 356/301 |
| 8,680,993 B2 | 3/2014 | Xu et al. |
| 8,735,803 B2 | 5/2014 | Ford et al. |
| 2007/0263213 A1 * | 11/2007 | Stedman .......... G01J 3/02 356/328 |
| 2008/0117405 A1 * | 5/2008 | Ridder .......... G01J 3/45 356/4.01 |
| 2011/0108720 A1 * | 5/2011 | Ford .......... E21B 49/08 250/262 |
| 2015/0362366 A1 * | 12/2015 | Tsuji .......... G01J 3/18 356/72 |
| 2016/0334274 A1 | 11/2016 | Xu |
| 2017/0122874 A1 * | 5/2017 | Alon .......... G01N 21/65 |

OTHER PUBLICATIONS

Researchgate Portable Optical Spectroscopy for Accurate Analysis of Ethane in Exhaled Breath Dated Jan. 30, 2017 (7 pages).
Infrared Physics & Technology "A Near-Infrared Acetylene Detection System Based on a 1.534 um Tunable Diode Laser and a Miniature Gas Chamber" Dated Jan. 6, 2016 (7 pages).
Savannah River National Laboratory "Spectrophotometers for Plutonium Monitoring in HB-Line" Dated Feb. 12, 2016 (72 pages).

* cited by examiner

FIG. 6 though the spectrometers may have identical designs, their wavelength-to-pixel calibrations will not be identical and are subject to wavelength drift typically associated with temperature changes and component aging. Over time the wavelength calibration of the two spectrometers drift apart. Therefore, in order to function accurately, there must be a way to convert the wavelength-to-pixel calibrations for the sample and reference spectrometers to a common basis for accurate comparison. Similarly, corrections must be made to assure that the response to intensity changes is proportionally identical for both spectrometers.

HIGH ACCURACY ABSORBANCE SPECTROPHOTOMETERS

STATEMENT REGARDING FEDERALLY SPONSORED RESEARCH OR DEVELOPMENT

This invention was made with government support under Contract No. DE-AC09-08SR22470 and under Contract No. DE-AC09-96SR18500 awarded by the U.S. Department of Energy. The government has certain rights in the invention.

BACKGROUND

Spectrophotometers are useful in many analyte detection regimes as they can continuously and simultaneously measure the result of light-matter interaction at multiple wavelengths. The interaction usually takes the form of absorbance as light is transmitted through the sample, but may also apply to changes as the light is scattered from the sample, or emission of light as a result of light incident upon the sample. Of these interactions, light absorbance is a particularly useful method. The wavelengths at which an analyte absorbs light is indicative of the type of analyte, and the amount of light absorbed at these wavelengths is proportional to that analyte's concentration. These features of absorbance are intrinsic to the analyte and are theoretically independent of the measurement instrument. It is these features that can allow for the application of sophisticated mathematical analysis techniques to establish accurate determination of analyte concentrations over a wide range of states or conditions of the analyte. These capabilities are described in the literature, for example see Baylor and O'Rourke (L. C. Baylor and P. E. O'Rourke, "UV-Vis for On-Line Analysis", in "Process Analytical Technology", K. A. Bakeev, Ed., Blackwell Publishing, Oxford, U K, 2005, Ch. 6).

Unfortunately real instruments distort measurement of intrinsic absorbance features by what is commonly known as the instrument response function. In some situations this function can be determined and can be used to correct measurements back to theoretical values. However the function is not constant but can drift over time. The multi-wavelength capability of spectrophotometers can allow for real-time diagnostics that can better correct for drift of the instrument response function.

Another advantage of the spectrophotometer is that by measuring absorbance at multiple wavelengths, a great deal of information can be acquired that can be used to distinguish various sources of signal changes. These capabilities allow the spectrophotometer to be used in situations where the properties of the sample may be changing over time, e.g. as a monitor for a particular analyte in a chemical process. As a result of such capabilities, for certain systems the accuracy of analyte detection and measurement with spectrophotometers can be higher than with other detection approaches.

Elements of spectrophotometer design such as hardware, control software, and data analysis technique are chosen to maximize these advantages and minimize instrument response effects. For example, spectrophotometers for absorbance or reflectance measurements generally include two spectrometers. One spectrometer is utilized as a reference spectrometer and is dedicated to monitoring the incident light intensity. The other spectrometer measures the light intensity after interaction with the sample. The sample spectrometer readings can be corrected for variations in the incident light intensity by dividing them by the reference spectrometer readings. Thus, overall intensity drift is corrected and changes in instrument output can be better correlated to changes in the sample.

Unfortunately, there are also difficulties in utilizing spectrophotometers. For instance, in many applications, there is no capability to calibrate/validate instrument performance in-line with a process operation. As such, there may be no way to continually monitor and confirm the instrument performance and calibration without uninstalling the spectrometers, or at least interrupting process operations in order to perform instrument checks.

Accurate calibration and validation of a spectrophotometer is not merely desirable from the standpoint of optimizing performance, however. It is critical for the instrument to work properly. Calculating sample absorbance requires comparison of the intensities of the same wavelengths from the two spectrometers and even What are needed in the art are spectrophotometers that can more accurately detect analytes and measure their concentrations. More specifically, spectrophotometers that can be accurately calibrated for each spectral acquisition and continuously correct for wavelength and intensity drift so as to provide spectral data of an "ideal virtual instrument", free of instrument response effects, would be of great benefit. Moreover, the ability to provide such on-going calibration and continuous correction while maintaining a spectrophotometer in-line would be highly beneficial.

SUMMARY

According to one embodiment, disclosed is a spectrophotometer that can include internal wavelength and/or intensity calibration systems so as to provide highly accurate absorbance, reflectance, and/or emission spectra, which are the basis for accurate analyte detection and quantitation. Also disclosed are methods for calibration of the spectrophotometers and for correction of spectrometer sample data for one or both of wavelength drift and for intensity drift.

A spectrophotometer can include a first light source that emits light over a first wavelength range. The emission of this light source can include a plurality of characteristic atomic emissions. More specifically, the frequencies of the characteristic atomic emissions can be fundamental, invariant properties of the source (e.g., a xenon lamp). The spectrophotometer can also include a second light source that emits light over a second wavelength range. As such, the two light sources can have complementary output ranges and can together provide a reasonably consistent intensity over a wavelength range of interest (which can vary depending upon the particular application and analyte).

The spectrophotometer can also include a beam splitter that can combine and split the light from the two light sources to form a sample beam that exits the beam splitter from a sample port and a reference beam that exits the beam splitter from a reference port.

Downstream of the sample port, the spectrophotometer can include a sample cell that is in optical communication with the sample port and a sample spectrometer that is in optical communication with the sample cell. Thus, a sample beam can travel from the sample port to the sample cell and the light emerging after the interaction with the sample is returned to the sample spectrometer. The spectrophotometer can also include a reference spectrometer that is downstream of and in optical communication with the reference port of the beam splitter. The sample and reference spectrometers can each include a detector (e.g., an array of photoelectric diodes or pixels) as are known in the art.

The spectrophotometer can also include a processor that is in communication with the spectrometers. The processor can be configured to manipulate input data from the spectrometers so as to calibrate each spectrometer and apply to sample data any necessary corrections as determined by the calibrations. The calibration process for each spectrometer can include carrying out analyses of detector responses in order to identify and map characteristic atomic emissions of the first light source to particular responses of each of the sample and reference spectrometer detectors. This mapping can allow for corrections that can then be applied during sample processing to convert the sample data from each spectrometer to a common basis (set of wavelengths). The processor can then determine an absorbance spectrum during sample processing by comparing the corrected raw data at identical wavelengths from each spectrometer.

The spectrophotometers and spectroscopy processes can also provide for intensity calibrations and corrections so as to assure that response to light intensity changes is proportionally identical (or nearly identical) for both the reference and sample spectrometers. For instance, a spectrophotometer can include an attenuator in the reference channel (i.e., downstream of the beam splitter and upstream of the reference spectrometer), that can assure that the overall intensity of the light is consistent across both the sample and reference spectrometers in the absence of a sample in that arm of the spectrophotometer. A spectrophotometer can also be designed to correct for response nonlinearities due to one or more of dark current, stray light, and order overlap, among others.

Through use of the instruments and methods, the wavelength and intensity measurement properties of individual spectrometers can be made equivalent to the properties of a virtual, ideal spectrometer. This equivalence allows for calculation of the absorbance spectrum of the sample from the measurements. The equivalence also assures that the data from different spectrophotometers of the same type can be directly compared with high confidence. It also assures that analyte detection models developed with data from one spectrophotometer can be used without correction to interpret data obtained with other spectrophotometers of the same type. Thus models developed in a laboratory setting can be used directly in a fielded instrument with no loss of accuracy, among other benefits.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In general, the present disclosure is directed to spectrophotometers and spectroscopy processes that can provide for highly accurate analyte detection and measurement. More specifically, the spectrophotometers and methods can provide for in-line calibration at every spectral acquisition as well as for continuous response correction during sample processing. As such, the spectra obtained can be highly accurate and consistent across time and between different spectrophotometers.

The disclosure may be applied equally to measurements based on: sample absorbance, wherein light is transmitted through the sample; reflectance, wherein light is scattered from the sample; or emission techniques where light is emitted from the sample as a result of interaction with the incident light. Examples of the latter include, but are not limited to, fluorescence, luminescence, and Raman spectroscopies. These examples will be evident to practitioners of the art. For the purposes of this disclosure, the example of absorbance spectroscopy will be used.

The spectrophotometers have been designed to incorporate an internal wavelength drift calibration system that is independent of environmental factors and that is independently applicable to all spectrometers of a spectrophotometer. The internal and independent nature of the wavelength response calibration provides for on-going calibration, for instance prior to every spectral acquisition. Moreover, the correction data provided by a calibration process can be applied continuously and across an entire sample spectrum. In conjunction with calibration and correction of wavelength response, the intensity response of each spectrometer in a spectrophotometer can be monitored and corrected for effects such as stray light, dark current, and readout noise. This can expand the accuracy of an instrument when measuring both small and large absorbance. Beneficially, by use of disclosed systems and methods, the absolute accuracy of an instrument's absorbance measurements can be quickly and easily confirmed, for instance by the measurement of National Institute of Standards and Technology (NIST)- traceable general absorbance standards. Application of analyte-specific calibrations to the confirmed absorbance measurements leads to highly accurate measurements of the analyte.

The absorbance measurement for a given sample can be determined from the light intensities of each spectrometer in a spectrophotometer by the following relationship:

$$A(\lambda)=\log_{10}[I(\lambda)/I_0(\lambda)]$$

in which $A(\lambda)$ is the absorbance at wavelength $\lambda$, $I_0(\lambda)$ is the incident light intensity at wavelength $\lambda$, $I(\lambda)$ is the transmitted light intensity at wavelength $\lambda$.

The concentration of analytes within the solutions can be determined by use of the Beer-Lambert Law, which describes the relationship between absorbance (A) and concentration according to the following:

$$A(\lambda)=\Sigma_i[\varepsilon_i(\lambda)\cdot b\cdot c_i]$$

in which $A(\lambda)$ is the absorbance at wavelength $\lambda$, $\varepsilon_i(\lambda)$ is the wavelength-dependent molar absorptivity of species i, b is the distance that the light travels through the solution of the species, c is the concentration of species i in the solution.

The Beer-Lambert Law can only be effectively applied to determine analyte concentrations if the identities of all species i in the solution are known, and if the molar absorptivities $\varepsilon$ are known for each species at the wavelengths used in the calculation. For instances in which these factors are not known, concentrations may still be determined by alternate statistical techniques. These techniques establish correlations between features of the absorption spectrum and analyte concentrations based on measurements of a calibration set of samples of known composition which are representative of the sample and conditions to be measured. A summary of the various techniques can be found readily in the literature, for example see Miller (C. E. Miller, "Chemometrics in Process Analytical Chemistry", in "Process Analytical Technology", K. A. Bakeev, Ed., Blackwell Publishing, Oxford, U K, 2005, Ch. 8).

These various methods of analyte calibration are known to ordinary practitioners of the art and are outside the scope of this disclosure. The claims and benefits contained within this disclosure apply equally to the two methods described above.

Disclosed spectrophotometers can be utilized in detection of analyte presence and concentration through determination of the absorbance information according to this relationship. The absorbance information, in turn, can be obtained through detection of the incident and transmitted light intensities at each particular wavelength of a spectrum. The combined wavelength and intensity calibrations and corrections provided by the disclosed devices and methods can be robust enough to make the responses from different spectrophotometers look as if they came from the same instrument. Such an "ideal virtual instrument" capability has several advantages. For instance, replacement instruments can be quickly installed without loss of quality or loss of response confidence. New analyte calibrations, for example to accommodate a change in the process conditions outside the original scope, can be developed in the laboratory using an instrument of this type and applied to multiple other spectrophotometers of this type with high confidence and with minimal impact on existing operations.

Figure 1:
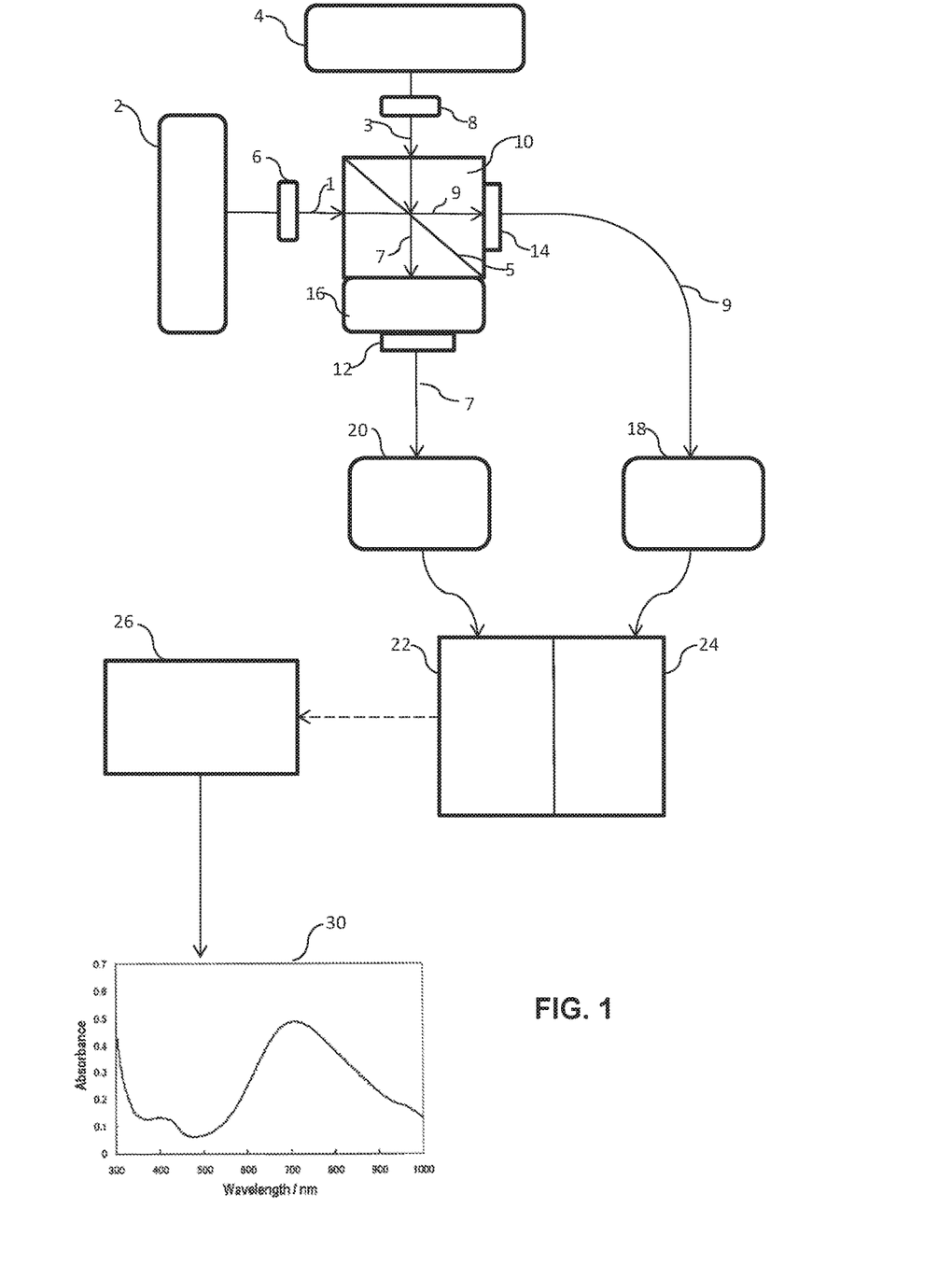
FIG. 1 schematically illustrates one embodiment of a spectrophotometer as described herein.

One embodiment of a spectrophotometer as disclosed is presented in FIG. 1. As can be seen, the spectrophotometer can include two light sources 2, 4, each of which providing polychromatic light across all or a portion of one or more of the ultraviolet (UV), visible (Vis), and infrared (IR) spectral ranges. For instance, each of the light sources can emit light across at least a portion of the visible spectrum (about 400 nm to about 700 nm) as well as light falling within one or both of the UV spectrum (about 200 nm to about 400 nm) and the IR spectrum (about 700 nm to about 2000 nm). The combination of the two light sources can be selected so as to provide a relatively even intensity distribution over the full wavelength range of interest. As such, the emission spectra of the two light sources 2, 4 can generally overlap at least partially, but this is not a requirement so long as there are intrinsic wavelength standards covering the full wavelength range of the measurement. For instance, in one embodiment, both light sources can emit light across the entire visible spectrum.

In general, the light sources 2, 4 can be commercially available light sources. In one particular embodiment, the first light source 2 can be a xenon lamp and the second light source 4 can be a tungsten-halogen lamp, as are known in the art and commercially available. The combination of a xenon lamp 2 and a tungsten-halogen lamp 4 can provides advantages for stable, long term operation as these lamps have complementary output ranges, with the tungsten lamp dominant for $\lambda$>500 nm, and together provide reasonably consistent intensity over many wavelengths desirable in general absorbance spectroscopy. In addition, both xenon and tungsten-halogen lamps have long lifetimes (many thousands of hours), and when combined with the calibration and correction capabilities of disclosed spectrophotometers, any emission degradation that does take place can affect both the reference and sample channels equally and can be compensated for in data processing.

Figure 2:
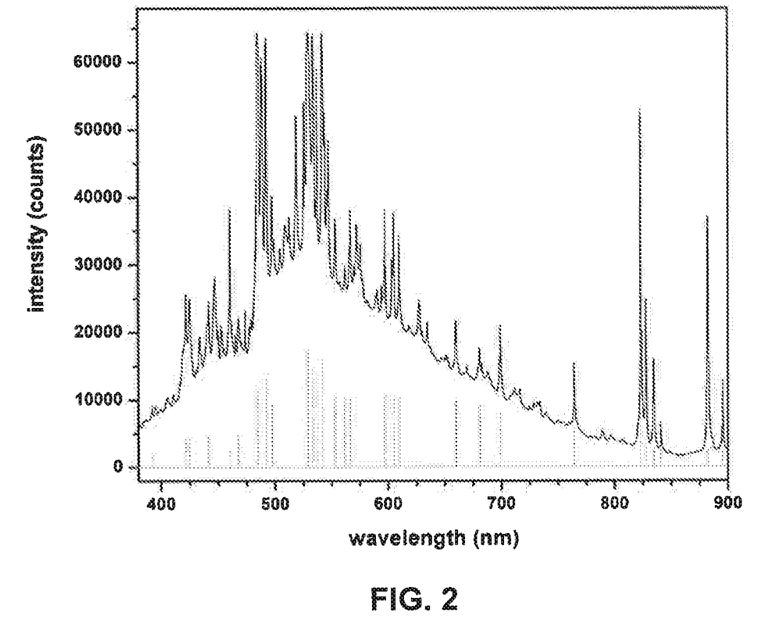
FIG. 2 illustrates the output of a xenon flash lamp and the reference wavelength emissions from xenon atoms.

One or both of the lamps is selected so as to provide internal wavelength standards that are used for the intrinsic instrument calibration (intensity vs. wavelength) in real time, improving stability and accuracy. More specifically, the emission of one or both of the lamps 2, 4 can contain a number of sharp emission lines that can serve as internal wavelength standards for calibration of the spectrometers. The frequencies of these lines are fundamental, invariant properties of the atoms comprising the emitting material of the lamp and as such can be used as calibration standards that will be independent of environmental factors due to the device and/or the testing environment. For instance, in one particular embodiment, the lamp source 2 can be a xenon lamp, the emission of which includes a number of sharp emission lines across the visible spectrum, as shown in FIG. 2. The upper trace of FIG. 2 shows the output of a xenon flash lamp as may be incorporated in a spectrophotometer. The lower trace illustrates the expected position of selected xenon atomic emission lines. Other light sources that may be used to provide standard emission lines include, but are not limited to, neon, argon, krypton, and mercury lamps.

Downstream of the light sources 2, 4, the spectrophotometer can include a beam splitter 10. At the spectrophotometer, the outputs 1, 3 of the light sources 2, 4 can be combined and split into a sample beam 7 and a reference beam 9. In general, the light 1, 3 from the light sources 2, 4, can be collimated and optionally, the system can include source balancers 6, 8, e.g., adjustable, lockable irises, that can regulate the source intensities.

At the beam splitter 10, the collimated beams of light 1, 3 from each lamp 2, 4 can be combined in the beam splitter

10. The beam splitter can contain a window 5 that is partially reflective and partially transmissive. In general, the window 5 can be half reflective and half transmissive so as to split the combined light 1, 3 in a 50/50 split. This is not a requirement, however, and in some embodiments it may be preferred to form a different, non-equal split of the source light.

The beam splitter 10 can include a sample port 12 and a reference port 14 through which the sample beam 7 and the reference beam 9 exit the beam splitter. The sample beam 7 can pass to the sample cell 20, for instance by coupling to an optical fiber as is known and then on to a sample spectrometer 22. The sample beam 7 can optionally pass through other components 16, such as filter slots, cuvette holders, etc., that can be combined together along the travel path of the sample beam 7 or separated, as desired. For instance, a check filter slot can accept a check filter with known absorbance properties when it is activated, and a cuvette holder can accept other absorbance standards as are generally known in the art and that can be used to verify the calibration of the instrument. Under normal operation, such additional components 16 are generally empty.

The reference beam of light 9 exiting the beam splitter 10 at the reference port 14 can likewise be coupled into an optical fiber and, after passing through any additional control mechanisms 18 (details and examples of which are discussed further herein), can pass to the reference spectrometer 24.

Data obtained at both spectrometers 22, 24 are communicated to a processing unit 26 through the communications ports as are generally known in the art. The system can include additional components as are known in the art including, without limitation, power supplies including ac/dc converters and the like to supply the spectrometers, lamps, communication ports, check filter mechanism, etc.

The spectrometers 22, 24 can include any suitable spectrometers as is known in the art, however data collection from each of the spectrometers can be synchronized to effectively correct for intensity fluctuations of the light sources. For example, in one embodiment the spectrometers 22, 24 can be diode array spectrometers. As is known, diode array spectrometers operate by dispersing the incoming light with a grating and projecting the dispersed light onto a diode array detector. Each photoelectric diode in the array (generally referred to herein as a pixel) is designed to emit an electrical response to light intensity over a narrow range of wavelengths. The output of the spectrometer is thus a spectrum of intensities sampled at a discrete number of points, each of which representing a narrow band of wavelengths. The intensity measured at each pixel is assumed to represent the intensity at the center wavelength of that band. However, the spectrometers are not limited to diode array spectrometers, and any other detection mechanism as is known in the art that provides independent intensity vs. wavelength data for the reference and sample arms of the instrument can be utilized in the disclosed systems.

In general, the spectrometers 22, 24 of a system can be rugged with no moving parts. However, all spectrometers may be subject to small irregularities that can limit the accuracy of the spectra it obtains. For example, thermal expansion can alter the wavelength calibration. As such, disclosed devices incorporate a wavelength calibration that can correct spectral acquisitions for such irregularities.

The wavelength calibration technique includes identification of spectrometer responses to characteristic atomic emissions of the first light source 2 and to correlating these characteristic emissions to particular detector responses of each of the sample spectrometer 22 and the reference spectrometer 24. For instance, in those embodiments in which the spectrometers include a pixel array, the correlation can include mapping each characteristic emission to an electrical response of a particular pixel of the diode array.

Through comparison and interpolation of the correlation results for both spectrometers 22, 24, corrections can be established that can be carried out during sample analysis. Advantage of the wavelength calibration is two-fold. First, the correlation (e.g., mapping of characteristic emission wavelength to pixel) will generally not be identical for the reference and sample spectrometers. In order to provide accurate data, the intensity spectra should be harmonized (corrected) so that the intensities from the two spectrometers 22, 24 at identical wavelengths and times are used to calculate the absorbance spectrum. Second, the fundamental nature of the emission lines that are used as the calibration standard means that not only the spectrometers of a single spectrophotometer unit, but spectrophotometers in different spectrophotometer units can be calibrated to the same standard. Therefore, the corrected spectra obtained from different units should be very similar (given similar corrections to the intensities as discussed herein). This can provide for instrument interchangeability and simple calibration transfer as well as other advantages.

As stated in the discussion of the light sources, at least one of the light sources 2 emits atomic emission lines that have well-characterized and invariant wavelengths that can be used as calibration signals. These emission lines can also be very narrow, e.g., less than about 0.01 nm, which can enhance measurement precision. The spectrometers 22, 24 can have enough wavelength resolution so that individual lines used in the calibration can be distinguished, and will not be blurred together. It also can have enough discernment (e.g., small number of wavelengths per pixel) that, despite the narrowness of the calibration signals, each emission peak can be encompassed by multiple detector responses (e.g., pixel responses). While the spectral resolution can be larger than the intrinsic peak width of the calibration signals, it can be less than the separation of the emission lines used in the calibration (see FIG. 2). As such, there can be multiple resolvable peaks across the spectrum of interest that can be used in the wavelength calibration. These conditions can be satisfied if the spectral resolution of the spectrometers is at least twice as large as the pixel spacing, and the separation between chosen emission lines is at least twice the spectral resolution.

In general, spectrometers for use in a spectrophotometer can include detectors that have a spectral resolution of from about 0.3 nm to about 0.5 nm, for instance about 0.4 nm. The wavelength range of the spectrometers can generally depend upon the specific application, but in general can be from about 200 nm to about 1100 nm, for instance from about 375 nm to about 875 nm in one embodiment. The stray light (at 520 nm) can generally be less than about 0.1%, for instance from about 0.04 to about 0.1%. The sampling speed of the spectrometers can generally be about 10 ms/scan, for instance about 3.5 ms/scan to about 40 ms/scan. When considering pixel array-type spectrometers, the spectrometer can generally have a pixel spacing of from about 0.1 nm/pixel to about 0.2 nm/pixel and a total pixel count of about 2500 or greater (e.g., about 2500 to about 4000).

A procedure for a wavelength calibration can include real-time detection of the calibration signals (e.g., the xenon peaks), comparison of the measured and expected wavelengths of these signals, and application of any corrections determined by the wavelength calibration during sampling.

Figure 3:
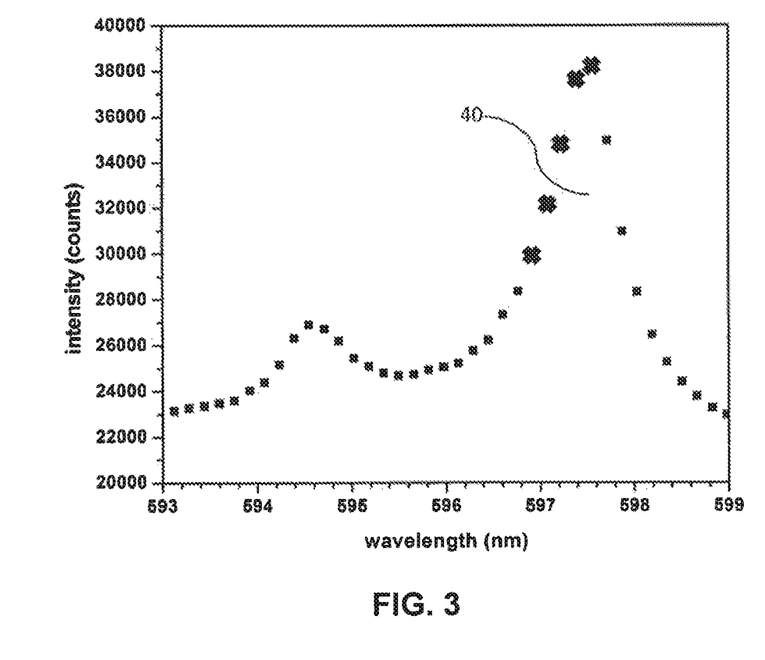
FIG. 3 illustrates an expanded portion of an intensity spectrum utilized during a wavelength drift calibration process.

By way of example, FIG. 3 illustrates an expanded portion of an intensity spectrum including a calibration signal 40 that corresponds to one of the characteristic atomic emissions of the light source 2. As shown, the spectrometer can have suitable discernment such that the calibration signal 40 is made up of multiple detector responses, presented on FIG. 3 as discrete points. To carry out a calibration, the following process can be carried out in a stepwise fashion for each discrete point in the spectrum (optionally excluding a number of leading and trailing pixels as describe below). A multi-point response window of a width of a fixed number of pixels can be defined for each point. The width of the window can vary, but in this embodiment is defined as 5 pixels (a pixel of interest, and two pixels before and after). Use of a window comprised of an odd number of pixels can be useful, as this can assure that the window is symmetric around a center point. In FIG. 3, a 5-point response window is shown with X-marked response points. The intensities at these five points can be subjected to spline interpolation and thereby fit to a quadratic equation, $$I(x)=a_0+a_1x-a_2x^2,$$

in which x is the position relative to the center of the window.

Alternately, the intensities at these five points can be subjected to spline interpolation and thereby fit to a Gaussian equation, $$\log(I(x))=a_0+a_1x-a_2x^2,$$

in which x is the position relative to the center of the window.

In this formulation, two conditions can be met to detect a calibration peak and determine its position. The first condition is that $a_2$ will be large and positive if there is a calibration peak present within the window. Thus, if the fit value of $a_2$ is below a threshold value, it is assumed that no peak is present, and the window is moved over one detection point (e.g., one pixel) and the evaluation process is restarted. The threshold value can depend upon the particular emission spectrum used for the calibration as well as the characteristics of the spectrometer. For instance, when considering a xenon lamp as the calibration emission spectrum source, the threshold value can be about 25. If $a_2$ is greater than the threshold value, the peak position is calculated using the equation, delta=$a_1/(2*a_2)$. This corresponds to the condition of the first derivative being equal to zero. The second condition for peak identification is that delta must be less than 1.

In this process, for a window of size 2n+1, then leading and n trailing pixels in the array will have windows that extend beyond the ends of the array. There are several approaches that may be taken to address peak scanning in these regions. In this embodiment, these regions are simply ignored, as they are known to not contain any emissions from the xenon wavelength standard. Other approaches as may be taken should that information be required will be known to those versed in the art.

In this way a table of peak positions can be formed. The rough wavelength values for the peaks can be estimated from an initial calibration for the instrument, e.g., the manufacturer's factory calibration. This allows each detected calibration signal to be identified with a particular detector response. For instance, each detected atomic emission line of a characteristic xenon emission can be mapped to a particular pixel of the spectrometer. The number of individual calibration signals can vary, and need not include every emission line of the light source. For instance, the calibration can include detection of about 10 or more calibration signals. In one embodiment a table can be refined to include about 30 xenon lines correlated to particular spectrometer responses.

This same mapping process can be carried out separately for both the sample spectrometer and the reference spectrometer, as each spectrometer will have a unique wavelength calibration. Accordingly, following this step, a calibration formula for each spectrometer can be determined that can correct the wavelengths of the recorded intensity spectrum to best reproduce the recognized wavelengths of the calibration standard. This process can assure that the wavelength values of the independent spectrometers are identical within the accuracy to which the calibration standard wavelengths are reproduced. Thus, the spectra from the two spectrometers can be compared with assurance that the selected wavelengths on each are essentially identical. For example, the calculation of the absorbance spectrum can be performed by comparison of the ratio of the sample and reference intensities at the same wavelength, as described above.

In one embodiment, the calibration formula for a spectrometer can be a third order polynomial of the form $$\lambda(x)=a_0+a_1x+a_2x^2+a_3x^3,$$

in which $\lambda(x)$ is the center wavelength of the $X^{th}$ pixel and the $a_i$ are coefficients resulting from the fit. An example of the calibration function obtained by this process and the reproduced values of the standard Xe emission lines is shown below, in Table 1.

TABLE 1

| Xe Line Table | | Hg—Ar Line Table | |
| --- | --- | --- | --- |
| Peak nm | LineSource | Peak nm | LineSource |
| 247.583 | Xe(II) | 253.652 | Hg_I |
| 260.504 | Xe(II) | 289.360 | Hg_I |
| 286.411 | Xe(II) | 296.728 | Hg_I |
| 297.721 | Xe(II) | 302.150 | Hg_I |
| 312.012 | Xe(II) | 334.148 | Hg_I |
| 362.424 | Xe(III) | 404.656 | Hg_I |
| 367.553 | Xe(III) | 407.784 | Hg_I |
| 372.008 | Xe(II) | 435.833 | Hg_I |
| 392.178 | Xe(III) | 491.607 | Hg_I |
| 421.560 | Xe(II) | 546.074 | Hg_I |
| 441.429 | Xe(II) | 576.960 | Hg_I |
| 460.297 | Xe(II) | 579.066 | Hg_I |
| 484.414 | Xe(II) | 690.746 | Hg_I |
| 492.108 | Xe(II) | 696.543 | Ar_I |
| 519.114 | Xe(II) | 706.722 | Ar_I |
| 526.173 | Xe(II) | 727.294 | Ar_I |
| 529.153 | Xe(II) | 738.398 | Ar_I |
| 533.849 | Xe(II) | 750.387 | Ar_I |
| 537.166 | Xe(II) | 751.465 | Ar_I |
| 541.873 | Xe(II) | 763.511 | Ar_I |
| 553.212 | Xe(II) | 772.376 | Ar_I |
| 566.825 | Xe(II) | 794.818 | Ar_I |
| 609.883 | Xe(II) | 800.616 | Ar_I |
| 634.492 | Xe(II) | 801.479 | Ar_I |
| 659.717 | Xe(II) | 810.369 | Ar_I |
| 669.573 | Xe(II) | 811.531 | Ar_I |
| 680.735 | Xe(II) | 826.452 | Ar_I |
| 699.249 | Xe(II) | 840.821 | Ar_I |
| 764.413 | Xe(I) | 842.465 | Ar_I |
| 823.373 | Xe(I) | 852.144 | Ar_I |
| 828.184 | Xe(I) | 912.297 | Ar_I |
| 834.800 | Xe(I) | | |
| 841.076 | Xe(I) | | |
| 882.169 | Xe(I) | | |
| 895.436 | Xe(I) | | |
| 904.728 | Xe(I) | | |
| 916.473 | Xe(I) | | |

TABLE 1-continued

| Xe Line Table | | Hg—Ar Line Table | |
|---|---|---|---|
| Peak nm | LineSource | Peak nm | LineSource |
| 979.918 | Xe(I) | | |
| 992.522 | Xe(I) | | |
| 1010.916 | Xe(I) | | |
| 1052.967 | Xe(I) | | |

The calibration process can match the characteristic emission peak positions with a root mean square (RMS) error of about 0.04 nm or less, for instance 0.02 nm, which, in one embodiment, can be about ⅛th of the spacing between pixels. This can compare favorably with the typical accuracy of factory calibration, which can be as high as 0.5 nm RMS error.

In addition to wavelength drift correction, a spectrophotometer can be calibrated and corrected in order to account for intensity drift errors. Intensity calibrations can assure that proportional changes to light intensity are accurately accounted for in all parts of the instrument response range. For instance, microscopic irregularities in the grating surface of a spectrometer can lead to light scattering ("stray light") within the device, so that a small fraction of the light of a particular wavelength can be incident on all pixels. The dominant sources of response nonlinearities at the low intensity end, leading to error in the absorbance measurement, are dark current and stray light. Another property of gratings (even ideal ones) allows for a spatial overlap of light with multiples ("orders") of the same frequency (for example, the pixel receiving 800 nm light can also receive a small fraction of 400 nm light). Electronic effects of the spectrophotometer or surrounding systems can lead to detector noise (at low signal levels) or nonlinear response (at high signal levels). The best quality spectrometers can minimize these effects, but disclosed spectrophotometers can provide for further correction in order to achieve higher measurement accuracy.

Referring again to FIG. 1, in one embodiment, a spectrophotometer can include as a component of a control mechanism 18 along the path of the reference beam 9 an attenuator in the form of, e.g., a controllable iris. In this embodiment, the reference beam 9 can be attenuated with the iris so that the overall intensity of the reference beam 9 is consistent with the light passing through the sample cell 20 and passing to the sample spectrometer 22. This balancing can allow the same integration times to be used for both instruments. Using the same integration time can provide two benefits. The dark current, described below, will be of a similar magnitude for both instruments, which helps assure that the instruments will have a similar response at low intensity levels. Also, this simplifies synchronization of the sample and reference spectrometers because the light sources 2, 4 can be measured over the same period of time. Source variation over that period can affect both instruments equally. Thus, the absorbance, which is proportional to the ratio of the signals from the two detectors, can be determined only by the absorbance of the sample and will not depend on the lamp source.

Dark current is a background electrical signal due to thermal excitation of electrons in the circuit. It can generate an offset signal that can be comparable to low incident light levels. In one embodiment to correct for dark current, several pixels at the end of the array of each spectrometer can be physically masked so that they are not exposed to light. These pixels can then be read to estimate the dark current, and the average of these responses can be subtracted from every spectrum as a dynamic dark correction.

Stray light is light of any wavelength which strikes a detector so as to generate a response that is not associated with this wavelength. It occurs mainly due to scattering from microscopic irregularities of the optical components (grating, mirrors) of the spectrometer. This effect can occur throughout the spectrum of the spectrometer but is more prevalent at shorter wavelengths. The amount of stray light in a system can be estimated by the use of a long-pass filter to prevent light at wavelengths below the filter cut-off from entering the spectrometer. Any light subsequently observed at the shorter wavelengths is therefore stray light of a longer wavelength. This light level is generally on the order of about 0.05% of the light intensity at longer wavelengths (e.g., about 20 counts out of 40,000). The amount of stray light will be essentially invariant with time and changes in environmental conditions for any spectrometer. Therefore, a one-time corrective formula, determined during instrument development, can generally suffice for future spectra. This formula can then be applied by the processor 26 during data acquisition.

Order overlap is separate effect that preferentially appears at longer wavelengths. This phenomenon is a property of gratings, in which harmonics of a given wavelength will be coincident on the same detector pixel. To counter this, the spectrometers 22, 24 can include internal "order-sorting" filters mounted in front of the pixel array. These filters are typically part of the specifications for the spectrometers used in these instruments. However, they can be added to the disclosed systems if they are not already in place.

An additional correction to the absorbance spectrum is required to account for the fact that the light paths from the light sources to the sample and reference spectrometers will not be identical, even with the use of the balancing iris. Differences can occur due to different lengths of optical fiber used in the two arms and by the presence of a flow cell in the sample path but not in the reference path. These differences result in an absorbance offset that will be independent of the sample in the flow cell and of the light sources that are used. This offset can be subtracted from any sample spectra. The offset is measured by obtaining the spectrum of a blank solution which does not contain the species being analyzed, or ideally any absorbing species. This offset is called a blank spectrum.

As previously discussed, disclosed spectrophotometers can optionally include other external standards as are generally known in the art. In one embodiment, at least two types of external standards can be used to certify the absorbance measurements of the spectrophotometers. The selected external standards can have characteristic absorption spectra and can include a highly mechanically and chemically stable metal oxide film with a protective quartz coating. By way of example and without limitation, external standards can be selected from metal-oxide neutral density filters and check filters.

Metal-oxide neutral density (ND) filters are grey filters that have a comparatively flat response across the visible spectrum. The absorbance values at specific wavelengths are traceable to the NIST and can be recertified by vendors who maintain ISO-certified programs. Holmium (Ho) oxide filters have characteristic peaks and are typically used as wavelength standards. In this embodiment, the filters can be used both as a check filter to provide an on-demand performance check and as a non-traceable absorbance measurement check.

As a check filter, a Ho oxide filter can generate an instrument response when inserted into the light path. The consistency of the response with the expected value, obtained when the instrument was initially calibrated, indicates that the instrument continues to work properly. The absorbance values for several peaks in the Ho oxide spectrum can also be used as an informal check of absorbance response. The check can be informal, because Ho oxide filters are not certified for absorbance, but the peaks can span a larger absorbance range than is available for the neutral density filters, and the information obtained thereby can be useful.

When utilized, a check filter can be inserted in the path of the sample beam 7 of the spectrophotometer, for instance as a component 16 downstream of the beam splitter 10. After passing through the filter, the sample beam 7 can pass through the sample cell 20 before entering the sample spectrometer 22. Therefore, checks are generally carried out with a recently flushed flow cell (and a new blank can be recorded if required) and with fibers in a stable position.

Optical fibers and flow cells can be standard as are known in the art. For instance, optical fibers can be UV-enhanced multimode fibers, with a 400 micron high-OH core, 440 micron doped silica cladding, Kevlar strength members, and an outer polyimide jacket as are known in the art and available in the market. Fibers can be terminated with SMA 905 connectors and rubber sleeves for strain relief.

A spectrophotometer can also include the processor 26 that can include software configured to control multiple aspects of a system including, without limitation, data acquisition and processing including control of the spectrometers and lamps, application of wavelength and intensity calibrations, and processing raw data to the "virtual instrument" basis, as well as evaluating diagnostics for system health and data quality;

Data processing can include transformation of the raw data communicated from the spectrometers 22, 24 to the processor 26 from an intensity versus pixel basis to an absorbance versus virtual wavelength basis. In one embodiment, processing can include correction of the intensity spectrum from each detector for one or more of dark current, stray light, second-order overlap, and detector non-linearity. Following, the detection responses (e.g., the pixel positions) can be converted to wavelengths, using the calibrated positions of the xenon emission lines as an internal standard. The sample and reference spectra can then be interpolated using a spline fitting algorithm to a standardized set of wavelengths (e.g., 200-1100 nm with 0.2 nm spacing, for a total of 4501 points). At this point, the reference and sample intensity spectra can be directly comparable. The absorbance at each corrected wavelength can then be calculated from the sample to reference intensity ratio. The final absorbance spectrum can then be calculated by subtracting the blank absorbance spectrum, which represents the apparent absorbance of the sample beam relative to the reference beam arising due to differences in the fiber lengths and the presence of the sample cell in the sample path. The corrected intensity data can also be used to construct diagnostic information useful for validating spectrophotometer performance. For instance the ratio of the current reference intensity to the blank reference intensity is a measure of the amount of lamp drift over time. This drift information can be used to predict remaining lamp lifetime.

The present disclosure may be better understood with reference to the Examples set forth below.

Example 1

The significance of the accuracy improvement that can be attained by the internal wavelength calibration described herein can be estimated by observing the effect on a typical analyte concentration determination associated with wavelength error.

Figure 4:
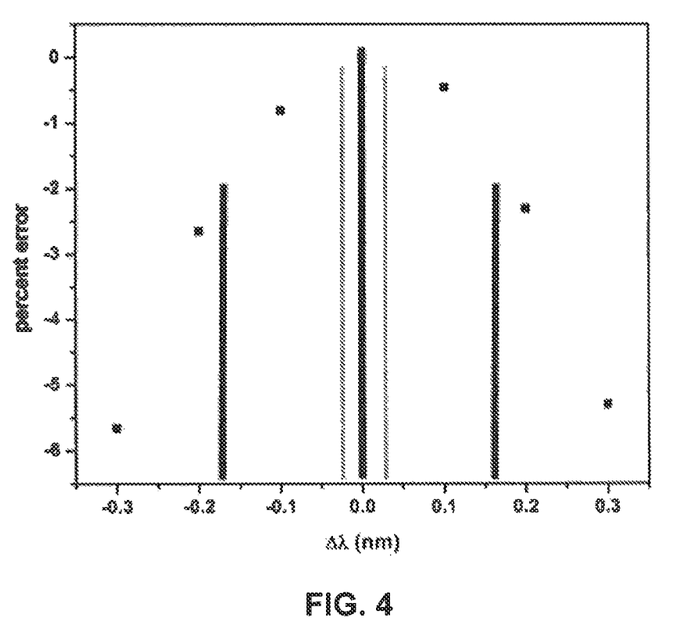
FIG. 4 demonstrates the effect of a wavelength calibration error on plutonium concentration prediction.

A calibration model based on statistical correlations was applied to otherwise identical plutonium (Pu) spectra that were shifted by fractions of a nanometer. The changes in the observed reading are shown in FIG. 4. A shift of ±0.02 nm from the true wavelength value, indicated by the light lines, corresponds to a 0.1% error in predicted value. The dark lines represent the positions of individual pixels. A 1-pixel error (~0.15 nm) corresponds to a Pu measurement error of −2%, and errors as large as ±0.3 nm (almost 2 pixels) correspond to a 6% Pu measurement error. Thus, rigorous wavelength calibration is critical for accurate Pu measurements.

Example 2

This example illustrates the significance of errors due to intensity effects.

The strongest absorbance peak for $Pu^{4+}$ is at about 475 nm. The intensity of a xenon lamp and tungsten-halogen lamp combined source at this wavelength will be approximately 20,000 counts on a typical spectrometer with typical integration times, with higher intensity at longer wavelengths. A solution absorbance of 2.2 at 475 nm would thus result in about 125 counts reaching the detector. However, an uncorrected stray light level at 475 nm equal to 0.05% of the longer wavelength light would add about 20 counts to the measurement, resulting in 145 counts at the detector. Therefore, the measured absorbance would be 2.14 ($\log_{10}$ (20,000/145)), which is a bias of about 3% from the true value. This potential bias is eliminated with the corrections described herein. The limiting factor for accurate measurement at high absorbance is therefore the random (thermal) detector noise, which provides a 1-sigma random uncertainty of about ±3 counts (roughly ⅓ the peak-to-peak noise of ±9 counts). For the present example, this corresponds to an absorbance uncertainty of 0.95% (range of A=2.194-2.215).

Example 3

Figure 5:
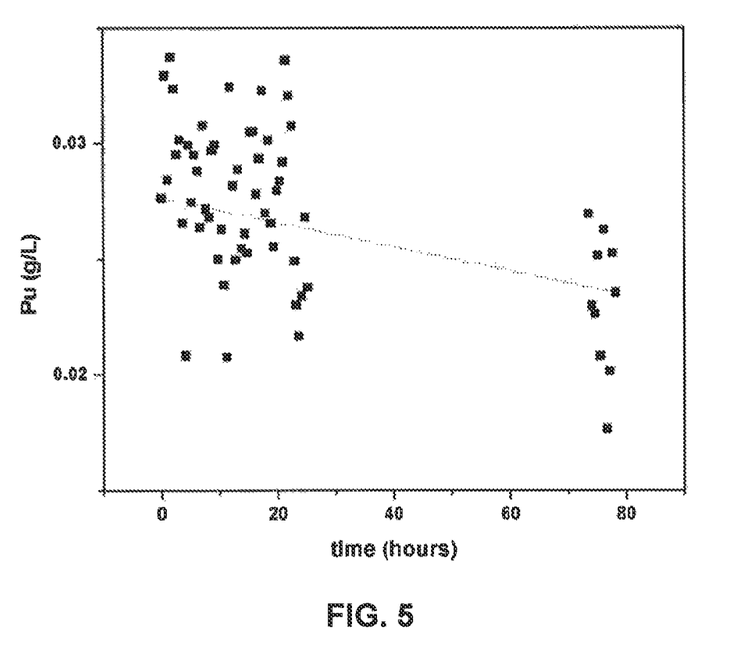
FIG. 5 illustrates zero drift observations for a spectrophotometer as described herein over a period of 80 hours.

The maximum zero shift is expected to be the same at all parts of a spectrometer scale. The maximum zero shift was determined on a spectrophotometer as described herein by repeated measurement of a low concentration Pu solution in nitric acid over 80 hours. Spectra were analyzed by a Pu calibration model based on statistical correlation. The overall standard deviation (1σ) for this set was 0.0036 g/L. The time dependence of the data is shown in FIG. 5. There was a slight overall downward trend to the data, indicated by the regression line, with an apparent rate of change of about $-8 \times 10^{-5}$ g/L/hr. The trend is much smaller than the spread of data, as indicated by the low regression value $r^2$=0.26. Analysis of the data up to t=25 hours shows no statistically significant drift. Information about the changes in laboratory conditions during this test was not available. The self-referencing design of the spectrophotometer explicitly measures and corrects for drifts in lamp color and intensity, and the data processing in the total Pu calibrations corrects for other effects associated with the fibers and flow cell. Therefore, the standard deviation observed for the data set is a more realistic measure of the variability of the blank/low level measurement.

Figure 6:
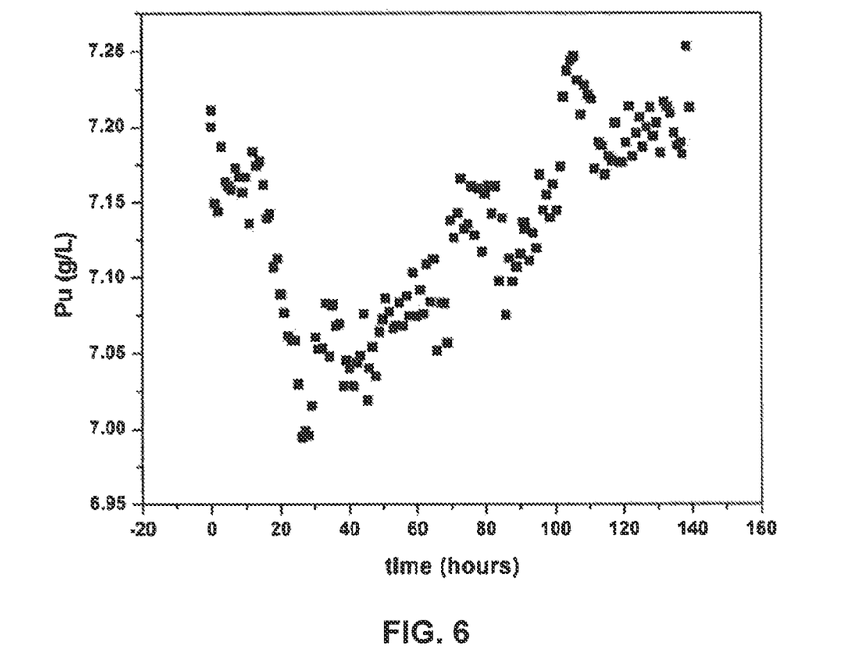
FIG. 6 illustrates long-term drift observations for measurement of plutonium concentration in a stable solution for a spectrophotometer as described herein over a period of 5.8 days.

Long term output drift was also examined. This quantity is a proportional value. Long term output drift was determined by measuring the concentration of a Pu-containing nitric acid solution held in a sealed cuvette over 5.8 days. The results of the measurement are shown in FIG. 6. The standard deviation (1σ) of the measurement over this time is 0.062 g/L, or 0.9% of the mean measurement. It should be noted that the laboratory temperature varied by at least 10° C. over this period. The instrument reading tracked with temperature. A slight amount of condensation was observed at the top of the cuvette, which could be at least partially responsible for the observed change in Pu concentration.

Variability between instruments of the same type was also examined. Various spectrometers were paired to form 9 spectrophotometer systems, in configurations consistent with the embodiments described above. For each of these systems, absorbance measurements were made on a series of Pu-bearing standard solutions. A number of Pu calibration models were calculated based on the absorbance spectra from one of the systems. These models were each generated to apply to a subset of the total amount of Pu and nitric acid in the solution, as indicated in Table 2. The calibration models were then applied to the absorbance spectra measured with the other 8 instruments. Table 2 shows the variability of those results for each Pu model. The observed variability, between 0.6-3.4%, was very similar to the intrinsic accuracy of each model. These results demonstrate that the data obtained with independent virtual instruments of the type described herein are functionally identical, validating the principles of this creation.

TABLE 2

| | | Acid Range | | |
| --- | --- | --- | --- | --- |
| | | Low (0.3-2M) | Medium | High |
| | | $A_{830\,nm}$ <2.2 $\quad$ $A_{830\,nm}$ >2.2 | (2-6M) | (6-9M) |
| Absorbance | Low | σ = 1.33% $\quad$ σ = 1.90% | σ = 1.84% | σ = 0.63% |
| | Medium | σ = 1.78% $\quad$ σ = 3.37% | σ = 0.85% | σ = 0.61% |
| | High | σ = 1.27% | σ = 1.59% | σ = 1.00% |

While certain embodiments of the disclosed subject matter have been described using specific terms, such description is for illustrative purposes only, and it is to be understood that changes and variations may be made without departing from the spirit or scope of the subject matter.

What is claimed is:

1. A spectrophotometer comprising:
    a first light source configured to emit a first emission spectrum that spans a first wavelength range, the first emission spectrum comprising a plurality of characteristic atomic emissions;
    a second light source configured to emit a second emission spectrum that spans a second wavelength range;
    a beam splitter configured to combine light emitted from the first light source with light emitted from the second light source and split the combined light to form a sample beam and a reference beam;
    a sample cell downstream of and in optical communication with the beam splitter;
    a sample spectrometer downstream of and in optical communication with the sample cell;
    a reference spectrometer downstream of and in optical communication with the beam splitter; and
    a processor in communication with the sample spectrometer and the reference spectrometer, the processor being configured to map the characteristic atomic emissions of the first light source to a first set of responses of the sample spectrometer and to a second set of responses of the reference spectrometer, the processor being further configured to compare and interpolate the first set of responses with the second set of responses and to thereby obtain a correction function, the processor being further configured to apply the correction function to raw sample data communicated to the processor from the sample spectrometer and the reference spectrometer.

2. The spectrophotometer of claim 1, wherein the first light source comprises a xenon lamp.

3. The spectrophotometer of claim 1, wherein the second light source comprises a tungsten-halogen lamp.

4. The spectrophotometer of claim 1, the sample spectrometer comprising a diode array, the first set of responses comprising photoelectric responses of diodes of the diode array.

5. The spectrophotometer of claim 1, the reference spectrometer comprising a diode array, the second set of responses comprising photoelectric responses of diodes of the diode array.

6. The spectrophotometer of claim 1, further comprising light source balancers upstream of and in optical communication with the beam splitter.

7. The spectrophotometer of claim 1, wherein the beam splitter comprises a window that is half reflective and half transmissive to the combined light.

8. The spectrophotometer of claim 1, further comprising a check filter slot.

9. The spectrophotometer of claim 1, further comprising a light attenuator downstream of the beam splitter and in optical communication with the reference spectrometer.

10. The spectrophotometer of claim 1, further comprising one or ore external standards.

11. A method for determining an absorbance spectrum, the method comprising:
    combining a first emission spectrum of a first light source with a second emission spectrum of a second light source to form a combined spectra, the first emission spectrum comprising a plurality of characteristic atomic emissions;
    splitting the combined spectra to form a sample beam and a reference beam;
    directing the sample beam through a sample cell and to a sample spectrometer, the sample spectrometer developing a first data set in response to the sample beam;
    directing the reference beam to a reference spectrometer, the reference spectrometer developing a second data set in response to the reference beam;
    communicating the first and second data sets to a processor, the processor mapping the characteristic atomic emissions of the first light source to the first data set and to the second data set, the processor further comparing and interpolating the results of the mapping and thereby obtaining a correction function.

12. The method of claim 11, further comprising placing a sample in the sample cell and directing a second sample beam through the sample cell including the sample and to the sample spectrometer, the sample spectrometer developing a third data set in response to the second sample beam, the method further comprising communicating the third data set to the processor, the processor applying the correction function to the third data set and obtaining an absorbance spectrum for the sample.

13. The method of claim 12, further comprising subtracting a blank spectrum from the corrected third data set.

14. The method of claim 12, further comprising correcting the third data set for at least one of dark current and stray light.

15. The method of claim 11, wherein the plurality of characteristic atomic emissions comprise characteristic xenon emissions.

16. The method of claim 11, further comprising attenuating the reference beam.

17. The method of claim 11, wherein the step of mapping the characteristic atomic emissions of the first light source to the first data set and to the second data set comprises binning the first data set and the second data set into multi-point response windows and subjecting the multi-point response windows to spline interpolations.

18. The method of claim 17, wherein the multi-point response windows include a 5-point response window.

19. The method of claim 11, wherein the mapping results in development of 10 or more calibration signals from each of the first data set and the second data set.

20. The method of claim 11, wherein the correction function is a third order polynomial.

* * * * *

UNITED STATES PATENT AND TRADEMARK OFFICE
CERTIFICATE OF CORRECTION

| | | |
|---|---|---|
| PATENT NO. | : 10,151,633 B2 | Page 1 of 1 |
| APPLICATION NO. | : 15/428639 | |
| DATED | : December 11, 2018 | |
| INVENTOR(S) | : Patrick E. O'Rourke et al. | |

It is certified that error appears in the above-identified patent and that said Letters Patent is hereby corrected as shown below:

In the Claims

Column 16, Line 47:
"one or ore external standards."
Should read:
"one or more external standards."

Signed and Sealed this
Twenty-ninth Day of January, 2019

Andrei Iancu
*Director of the United States Patent and Trademark Office*